(12) United States Patent
Dabrowiak et al.

(10) Patent No.: US 9,314,370 B2
(45) Date of Patent: Apr. 19, 2016

(54) SELF-CENTERING PATIENT TEMPERATURE CONTROL CATHETER

(75) Inventors: Jeremy T. Dabrowiak, Redwood City, CA (US); Alex L. Lim, Santa Clara, CA (US); Venkata Vishnu Gurukula, Mountain View, CA (US); Richard A. Helkowski, Redwood City, CA (US)

(73) Assignee: Zoll Circulation, Inc., San Jose, CA (US)

( * ) Notice: Subject to any disclaimer, the term of this patent is extended or adjusted under 35 U.S.C. 154(b) by 1185 days.

(21) Appl. No.: 13/247,122

(22) Filed: Sep. 28, 2011

(65) Prior Publication Data
US 2013/0079856 A1   Mar. 28, 2013

(51) Int. Cl.
*A61F 7/00* (2006.01)
*A61F 7/12* (2006.01)

(52) U.S. Cl.
CPC ........... *A61F 7/12* (2013.01); *A61F 2007/0054* (2013.01); *A61F 2007/126* (2013.01)

(58) Field of Classification Search
USPC .................................................. 607/105–106
See application file for complete search history.

(56) References Cited

U.S. PATENT DOCUMENTS

| | | | |
|---|---|---|---|
| 1,459,112 A | 6/1923 | Mehl | |
| 1,857,031 A | 5/1932 | Schaffer | |
| 2,663,030 A | 12/1953 | Dahlberg | |
| 2,673,987 A | 4/1954 | Upshaw et al. | |
| 3,225,191 A | 12/1965 | Calhoun | |
| 3,369,549 A | 2/1968 | Armao | |
| 3,425,419 A | 2/1969 | Dato | |
| 3,504,674 A | 4/1970 | Swenson | |
| 3,726,269 A | 4/1973 | Webster, Jr. | |
| 3,744,555 A | 7/1973 | Fletcher et al. | |
| 3,751,077 A | 8/1973 | Hiszpanski | |
| 3,937,224 A | 2/1976 | Uecker | |
| 3,945,063 A | 3/1976 | Matsuura | |
| 4,038,519 A | 7/1977 | Foucras | |
| 4,065,264 A | 12/1977 | Lewin | |
| 4,103,511 A | 8/1978 | Kress et al. | |
| 4,126,132 A | 11/1978 | Portner et al. | |
| 4,153,048 A | 5/1979 | Magrini | |

(Continued)

FOREIGN PATENT DOCUMENTS

DE    19531935    2/1997
EP    1089780 B1    10/2012

(Continued)

OTHER PUBLICATIONS

F.W. Behmann, E. Bontke, "Die Regelung der Wärmebildung bei künstlicher Hypothermie", Pflügers Archiv, Bd. 266, S. 408-421 (1958).

(Continued)

*Primary Examiner* — Joseph Stoklosa
*Assistant Examiner* — Adam Avigan
(74) *Attorney, Agent, or Firm* — John L. Rogitz

(57) ABSTRACT

A patient temperature control catheter includes working fluid supply and return lumens through which working fluid circulates to exchange heat with a patient in whom the catheter is positioned. At least one lumen is defined by plural coils axially spaced from each other. At least a first coil is a large coil that inflates with working fluid to seat against a wall of a blood vessel in which the catheter is positioned, with blood flowing through the coil so as not to block blood flow in the vessel.

5 Claims, 3 Drawing Sheets

(56) References Cited

U.S. PATENT DOCUMENTS

| | | |
|---|---|---|
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,763,654 A | 8/1988 | Jang |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,334,346 A | 8/1994 | Kim et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,542,928 A | 8/1996 | Evans et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A * | 9/1999 | Dobak, III .................. 607/104 |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,485,500 B1 | 11/2002 | Kokish et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,589,271 B1 | 7/2003 | Tzeng et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaiuolo et al. |
| 6,635,076 B1 | 10/2003 | Ginsburg |
| 6,635,079 B2 | 10/2003 | Unsworth et al. |
| 6,679,906 B2 | 1/2004 | Hammack et al. |
| 6,685,733 B1 | 2/2004 | Dae et al. |
| 6,699,268 B2 * | 3/2004 | Kordis et al. .................. 607/105 |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,510,569 B2 | 3/2009 | Dae et al. |
| 7,666,215 B2 | 2/2010 | Callister et al. |
| 7,708,715 B2 | 5/2010 | Gellman |
| 7,770,584 B2 | 8/2010 | Danek et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0001832 A1 | 5/2001 | Dobak et al. |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0045925 A1 | 4/2002 | Keller et al. |
| 2002/0077665 A1 | 6/2002 | Kordis et al. |
| 2002/0111618 A1 | 8/2002 | Stewart et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0153845 A1 | 8/2003 | Emken et al. |
| 2003/0236496 A1 | 12/2003 | Samson et al. |
| 2004/0089058 A1 | 5/2004 | De Haan et al. |
| 2004/0102825 A1 | 5/2004 | Daoud |
| 2004/0210231 A1 | 10/2004 | Boucher et al. |
| 2005/0010273 A1 | 1/2005 | Walker et al. |
| 2005/0076924 A1* | 4/2005 | Dobak, III .................. 128/898 |
| 2005/0156744 A1 | 7/2005 | Pires |
| 2006/0004417 A1 | 1/2006 | Rossing et al. |
| 2007/0007640 A1 | 1/2007 | Harnden et al. |
| 2007/0076401 A1 | 4/2007 | Carrez et al. |
| 2008/0221651 A1 | 9/2008 | Dobak |
| 2010/0082012 A1 | 4/2010 | Hattangadi et al. |
| 2011/0130812 A1 | 6/2011 | Noda et al. |
| 2012/0259329 A1 | 10/2012 | DeCarlo |

(56) References Cited

U.S. PATENT DOCUMENTS

| | | |
|---|---|---|
| 2013/0079855 A1 | 3/2013 | Helkowski et al. |
| 2013/0079857 A1 | 3/2013 | Lim et al. |
| 2013/0178923 A1 | 7/2013 | Dabrowiak |

FOREIGN PATENT DOCUMENTS

| | | |
|---|---|---|
| GB | 2040169 | 8/1980 |
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| JP | 2011131094 | 7/2011 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0152781 A1 | 7/2001 |
| WO | 0164146 | 9/2001 |
| WO | 0176517 | 10/2001 |
| WO | 0183001 | 11/2001 |
| WO | 0236180 A2 | 5/2002 |

OTHER PUBLICATIONS

F.W. Behmann, E. Bontke, "Intravasale Kühlung", Pflügers Archie, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

Mark A. Saab, "Multi-Lumen Heat Transfer Catheter System", file history of pending U.S. Appl. No. 12/924,933, filed Oct. 8, 2010.

David J. Scott, Ben F. Brian, Lloyd F. Wright, Leo A. Chin, Edward W. Hollmen, Saniel W. Seegars, Mark A. Logan, "Apparatus and Method for Providing Enhanced Heat Transfer from a Body", file history of pending U.S. Appl. No. 12/897,637, filed Oct. 4, 2010.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,000, filed May 4, 2011.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,036, filed May 4, 2011.

Timothy R. Machold, Wade A. Keller, Alex T. Roth, Nicole Denise Bloom, "Method and System for Control of a Patient's Body Temperature by Way of a Transluminally Insertable Heat Exchange Catheter", file history of pending U.S. Appl. No. 13/161,648, filed Jun. 20, 2011.

Jeremy T. Dabrowiak, Alex L. Lim, Venkata Vishnu Gurukula, Masoumeh Mafi, "Self-Centering Patient Temperature Control Catheter" related pending U.S. Appl. No. 13/625,998 restriction requirement dated Jan. 26, 2015.

Jeremy T. Dabrowiak, Alex L. Lim, Venkata Vishnu Gurukula, Masoumeh Mafi, "Self-Centering Patient Temperature Control Catheter" related pending U.S. Appl. No. 13/625,998 applicants response to the restriction requirement filed Jan. 26, 2015.

Jeremy T. Dabrowiak, Alex L. Lim, Venkata Vishnu Gurukula, Masoumeh Mafi, "Self-Centering Patient Temperature Control Catheter" related pending U.S. Appl. No. 13/625,998 non-final office action dated Feb. 12, 2015.

Jeremy T. Dabrowiak, Alex L. Lim, Venkata Vishnu Gurukula, Masoumeh Mafi, "Self-Centering Patient Temperature Control Catheter" related pending U.S. Appl. No. 13/625,998 applicants response to the non-final office action filed Feb. 12, 2015.

\* cited by examiner

SELF-CENTERING PATIENT TEMPERATURE CONTROL CATHETER

I. FIELD OF THE INVENTION

The present application relates generally to patient temperature control systems.

II. BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146, 411, 6,019,783, 6,581,403, 7,287,398, and 5,837,003 (heat exchange systems for catheter), U.S. Pat. No. 7,857,781 (various heat exchange catheters).

SUMMARY OF THE INVENTION

Accordingly, a catheter includes at least one working fluid supply lumen and at least one working fluid return lumen. Working fluid circulates through the supply and return lumens to exchange heat with a patient in whom the catheter is positioned. At least one of the lumens is defined by plural coils axially spaced from each other. Furthermore, at least a first coil is a large coil that inflates with working fluid to seat against a wall of a blood vessel in which the catheter is positioned such that blood may flow through the coil so as not to block blood flow in the vessel. Thus, working fluid may flow serially through the coils to exchange heat with the patient.

In some embodiments, a second of the plural coils may be a smaller coil relative to the large coil, where the smaller coil does not contact the wall of the blood vessel when inflated with working fluid. Even further, if desired, at least one of the lumens may define plural large coils separated from each other by at least one small coil as described herein. Also if desired, at least one of the lumens may define a straight tube coaxial with the coils and in fluid communication with the coils. In non-limiting embodiments, the straight tube may extend through the coils, or may optionally be located outside the coils.

In some non-limiting embodiments, the coils may be in the working fluid supply path and the straight tube may define at least part of the working fluid return path. In other non-limiting embodiments, the coils may be in the working fluid return path and the straight tube may define at least part of the working fluid supply path.

In another aspect, a method includes circulating working fluid through working fluid supply and return lumens of a catheter to exchange heat with a patient in whom the catheter is positioned. The method also includes providing at least one self-centering member engaged with the catheter, where the member is expandable against a wall of a vascular area in which the catheter is positioned to center heat exchange regions of the catheter in the vascular area.

In still another aspect, a catheter includes working fluid supply and return lumens. Working fluid circulates through the supply and return lumens to exchange heat with a patient in whom the catheter is positioned. The catheter also includes at least one expandable wire located longitudinally along the catheter and engaged with the catheter. The wire is expandable against a wall of a blood vessel in which the catheter is positioned to center heat exchange regions of the catheter in the vessel.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
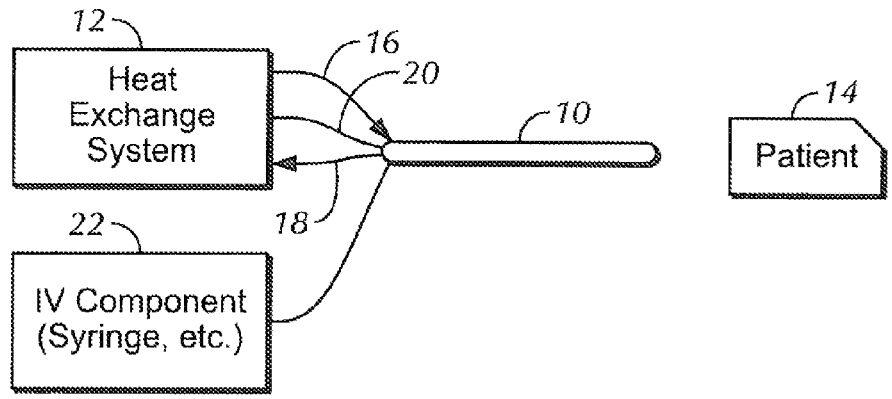
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic described in one or more of the patents referenced herein to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid may be circulated between the heat exchange system 12 and catheter 10 through supply and return lines 16, 18 that connect to the proximal end of the catheter 10 as shown. A patient temperature signal from a catheter-borne temperature sensor on the distal region of the catheter may be provided to the system 12 through an electrical line 20, or wirelessly if desired. Alternatively, a patient temperature signal may be provided to the system 12 from a separate esophageal probe or rectal probe or tympanic sensor or bladder probe or other temperature probe that measures the temperature of the patient 14. Note that as used herein, "proximal" and "distal" in reference to the catheter are relative to the system 12.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Next, regarding FIGS. 2-9, it is to be understood that while certain aspects and/or components of the example catheter described in reference to FIG. 1 have been omitted in FIGS. 2-9 for clarity, those aspects and/or components may still be present in the catheters described in reference to FIGS. 2-9 in non-limiting embodiments. For instance, the IV component, temperature sensor, and electrical line described in reference to FIG. 1 are not shown in FIGS. 2-9, but may still be included in the non-limiting embodiments shown in those figures.

Furthermore it is to be understood that distal heat exchange regions of the catheters as described herein may be made of a shape memory material such as, but not limited to, nitinol in non-limiting embodiments. Also in non-limiting embodiments, the shape memory material disclosed herein may expand and contract in accordance with present principles. However, it is to be further understood that the heat exchange regions as disclosed herein may be flexible and/or pliant in non-limiting embodiments such that distal regions of the catheters of FIGS. 2-6 may be flexibly positioned into a patient to exchange heat with a patient. E.g., the catheters described herein may flexibly enter the patient at an angle relative to the surface area of the portion of the patient in which the catheter is being positioned. Nonetheless, in other non-limiting embodiments the heat exchange region 32 may be rigid if desired.

Figure 2:
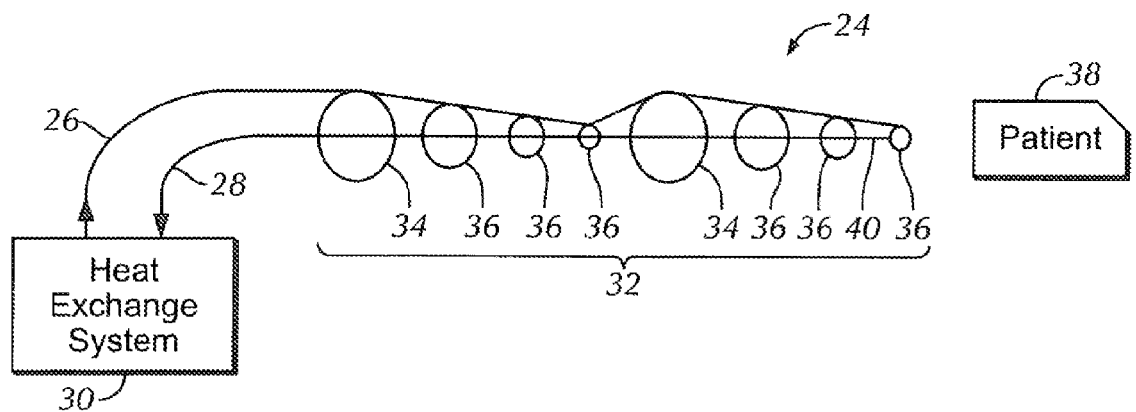
FIG. 2 is a schematic diagram of a non-limiting embodiment of the intravascular temperature management catheter having coils axially spaced from each other in accordance with present principles while not positioned in a patient.

Now specifically in reference to FIG. 2, a schematic diagram of an intravascular temperature management catheter while not positioned in a patient having coils axially spaced from each other in accordance with present principles is shown. Thus, a catheter 24 has a working fluid supply lumen 26 and a working fluid return lumen 28 in fluid communication with a heat exchange system 30 in accordance with present principles. Working fluid such as, but not limited to, saline may circulate through the lumens 26 and 28 to exchange heat with a patient 38 in whom the catheter 24 is positioned.

As may be seen from FIG. 2, at least one of the lumens 26 and 28 are defined by plural coils 32 axially spaced from each other, wherein at least one large coil 34 can inflate with working fluid to seat against a wall of a blood vessel (the vessel is not shown in FIG. 2) in which the catheter is to be positioned. FIG. 2 also shows at least one smaller coil 36, where the size of the smaller coil(s) 36 is relative to the large coil 34. The smaller coil(s) 36 may not contact the wall of the blood vessel when positioned in the patient 38 and inflated with working fluid in the non-limiting embodiment shown.

However, it may be appreciated from the non-limiting embodiment of FIG. 2 that the catheter 24 may have plural large coils 34 separated from each other by at least one of the smaller coils 36. Thus, while in some embodiments there may only be one large coil 34 and one smaller coil 36, FIG. 2 shows plural large coils 34 and plural smaller coils 36 such that working fluid may flow serially through the coils 32. Furthermore, it is to be appreciated from FIG. 2 that the smaller coils 36 may be of varying sizes, with all the smaller coils 36 still being smaller than the large coils 34.

Still in reference to FIG. 2, the catheter 24 may also have a straight tube 40 that may be both coaxial with the coils 32 and in fluid communication with the coils 32 in non-limiting embodiments. As shown in FIG. 2, the large coils 34 and smaller coils 36 are in the working fluid supply path 26, while the straight tube 40 defines at least part of the working fluid return path 28. However, it is to be understood that, in other non-limiting embodiments, large and smaller coils may be in the working fluid return path while the straight tube may define at least part of the working fluid supply path in accordance with present principles.

Figure 3:
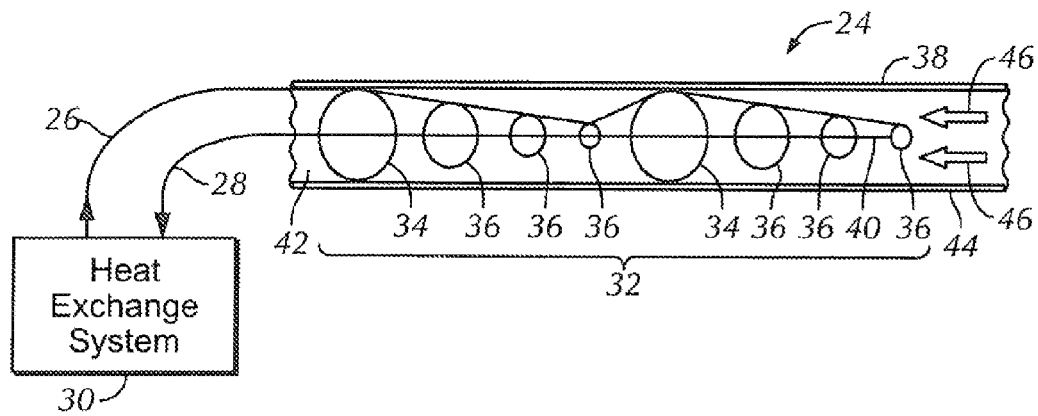
FIG. 3 is a schematic diagram of the non-limiting intravascular temperature management catheter of FIG. 2 while positioned in a patient.

Moving on to FIG. 3, a schematic diagram of the intravascular temperature management catheter 24 described in reference to FIG. 2 is shown, with the catheter 24 now positioned into a blood vessel 42 of the patient 38. Thus, the catheter 24 still has supply and return lumens 26 and 28 (and straight tube 40 defined by the lumen 28 in the non-limiting embodiment shown) which are in fluid communication with the heat exchange system 30. The catheter 24 also has large coil 34 and smaller coil 36 such that the plural coils 32 are axially spaced from each other.

It may be appreciated from FIG. 3 that the coils 32 are inflated with working fluid such that the large coils 34 are seated against the walls 44 of the blood vessel 42 in which the catheter 24 is positioned to center the smaller coils 36 in the blood vessel 42. As may be further appreciated from FIG. 3, the smaller coil(s) 36 may not contact the walls 44 of the blood vessel 42 while positioned in the blood vessel 42 and inflated with working fluid. Thus, blood may flow serially through the coils 32, as indicated by the blood-flow arrows 46, to exchange heat with the patient 38. It may also be appreciated that the coils 32 may be varying sizes such that they do not block the flow of blood through the blood vessel 42, while still providing optimum coil surface area to exchange heat with the patient 38.

Figure 4:
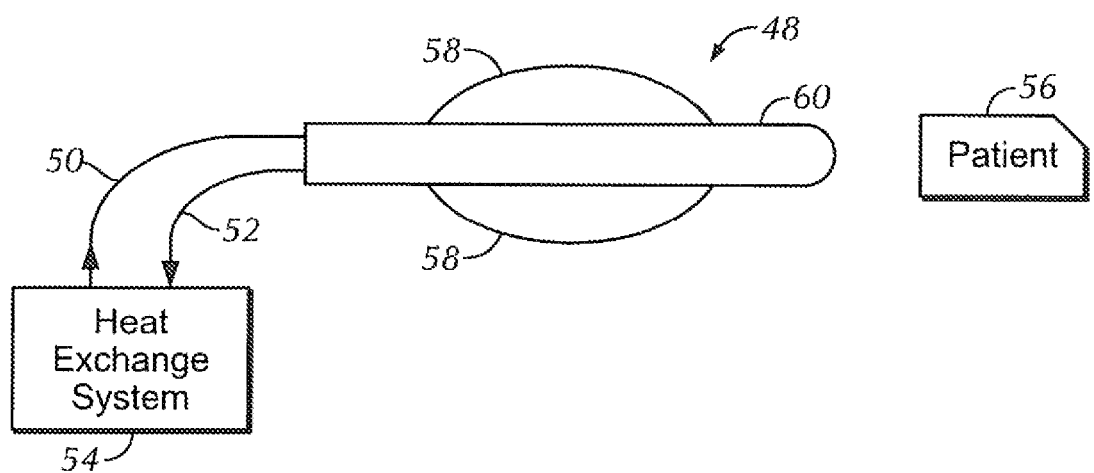
FIG. 4 is a schematic diagram of a non-limiting embodiment of the intravascular temperature management catheter while not positioned in a patient having at least one wire expandable against a wall of a blood vessel in which the catheter is positioned to center heat exchange regions of the catheter in accordance with present principles.

Now in reference to FIG. 4, another embodiment of a catheter in accordance with present principles is shown. Specifically, FIG. 4 is a schematic diagram of an intravascular temperature management catheter while not positioned in a patient having at least one wire expandable against a wall of a blood vessel in which the catheter is positioned to center heat exchange regions of the catheter to exchange heat with a patient.

Thus, as shown in FIG. 4, a catheter 48 has a working fluid supply lumen 50 and a working fluid return lumen 52 in fluid communication with a heat exchange system 54 in accordance with present principles. Working fluid such as, but not limited to, saline may circulate through the lumens 50 and 52 to exchange heat with a patient 56 in whom the catheter 48 is to be positioned. The catheter 48 also includes at least one expandable wire(s) 58 located longitudinally along the catheter 48 and engaged therewith. It is to be understood that the wire(s) 58 are expandable against a wall of a blood vessel of the patient 56 when positioned in the patient 56 to center a heat exchange region(s) 60 of the catheter 48 in the blood vessel (not shown). Note that plural wires 58 are shown in FIG. 4, where the plural wires 58 are engaged along the same longitudinal portion of the heat exchange region 60.

As understood herein, the wire(s) 58 may be made of a shape memory substance such as, but not limited to, nitinol. It is to be further understood that the heat exchange region(s) 60 may be substantially coaxial with the wire(s) 58 when the wire(s) 58 is expanded against the wall of the blood vessel, which may be further appreciated in FIG. 5 as described below. However, in other non-limiting embodiments, the wire(s) 58 need not be substantially coaxial with the heat exchange region(s) 60 as long as a portion of the wire(s) 58 may expand against the wall of the patient's blood vessel.

Figure 5:
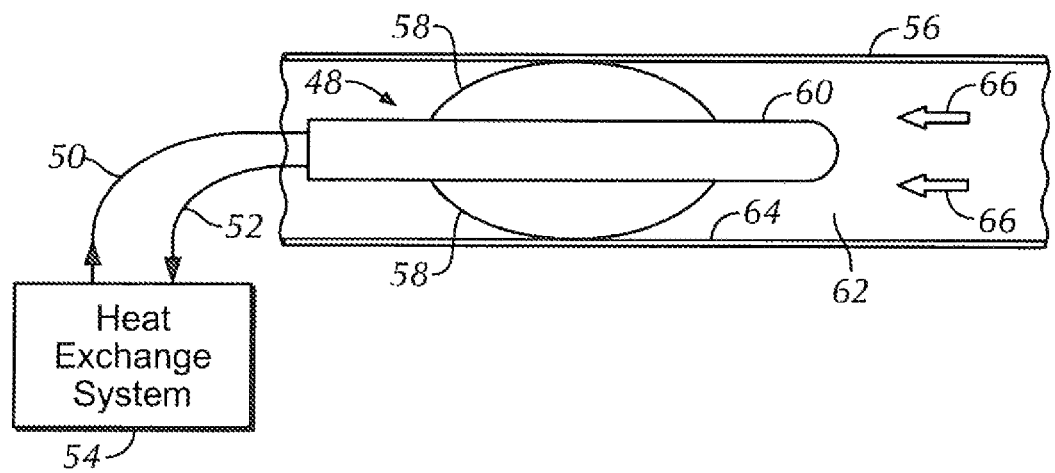
FIG. 5 is a schematic diagram of the non-limiting embodiment of the intravascular temperature management catheter of FIG. 4 while positioned in a patient.

Thus, FIG. 5 shows a schematic diagram of the intravascular temperature management catheter 48 described in reference to FIG. 4, with the catheter 48 now positioned into a blood vessel 62 of the patient 56. The catheter 48 still has the lumens 50 and 52 which are in fluid communication with the heat exchange system 54. The catheter 48 also has the wire(s) 58 which may be located generally longitudinally along the catheter 48 and engaged therewith.

It may be appreciated from FIG. 5 that a portion of the wire(s) 58 expands against the wall(s) 64 of the patient's blood vessel 62 to center the heat exchange region 60 in the blood vessel 62. Thus, blood may contact the heat exchange region(s) 60 as is passes the region(s) 60, as indicated by the blood-flow arrows 66, to exchange heat with the heat exchange region(s) 60.

Figure 6:
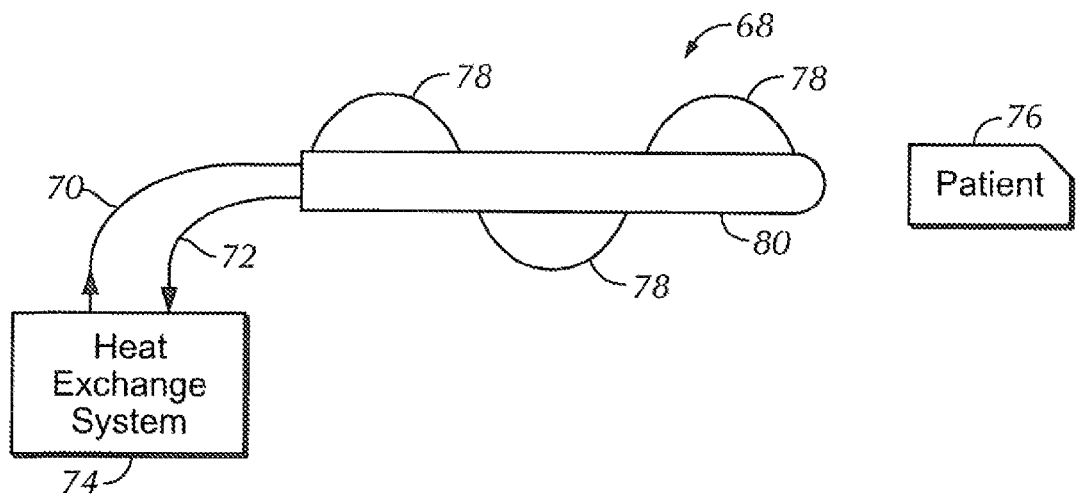
FIG. 6 is a schematic diagram of a second non-limiting embodiment of the intravascular temperature management catheter while not positioned in a patient having at least one wire expandable against a wall of a blood vessel in which the catheter is positioned to center heat exchange regions of the catheter in accordance with present principles.

Now in reference to FIG. 6, an alternate, non-limiting embodiment of a catheter in similar to the one described in reference to FIGS. 4 and 5 is shown. FIG. 6 also shows an intravascular temperature management catheter having at least one wire expandable against a wall of a blood vessel in which the catheter is positioned to center heat exchange regions of the catheter. However, the catheter shown in FIG. 6 includes plural wires that alternate longitudinally along the heat exchange region, where only one wire is engaged with only one longitudinal portion of the heat exchange region.

Thus, as shown in FIG. 6, a catheter 68 has a working fluid supply lumen 70 and a working fluid return lumen 72 in fluid communication with a heat exchange system 74 in accordance with present principles. Working fluid such as, but not limited to, saline may circulate through the lumens 70 and 72 to exchange heat with a patient 76 in whom the catheter 68 is to be positioned. The catheter 68 also includes expandable wires 78 located longitudinally along the catheter 68 and engaged with the catheter 68. It is to be understood that the wires 78 are expandable against a wall of a blood vessel of the patient 76 when positioned in the patient 76 to center a heat exchange region(s) 80 of the catheter 68 in the blood vessel (not shown).

As understood herein, the wires 78 may be made of a shape memory substance in accordance with present principles. It is to be further understood that the heat exchange region(s) 80 may be substantially coaxial with the wires 78 when the wires 78 are expanded against the wall of the blood vessel, which may be further appreciated in reference to FIG. 7 as described below. However, it is to be understood that in other non-limiting embodiments, the wires 78 need not be substantially coaxial with the heat exchange region(s) 80 as long as a portion of the wires 78 may expand against a wall of the patient's blood vessel.

In contrast to the embodiment described in reference to FIGS. 4 and 5, it may now be appreciated from FIG. 6 that the wires 78 alternate longitudinally along the heat exchange region 80 such that only one wire is included on only one longitudinal portion of the heat exchange region 80. The longitudinally alternating wires 78 can also been seen in reference to FIG. 7, where FIG. 7 is a schematic diagram of the catheter 68 while positioned in the blood vessel of the patient 76.

Figure 7:
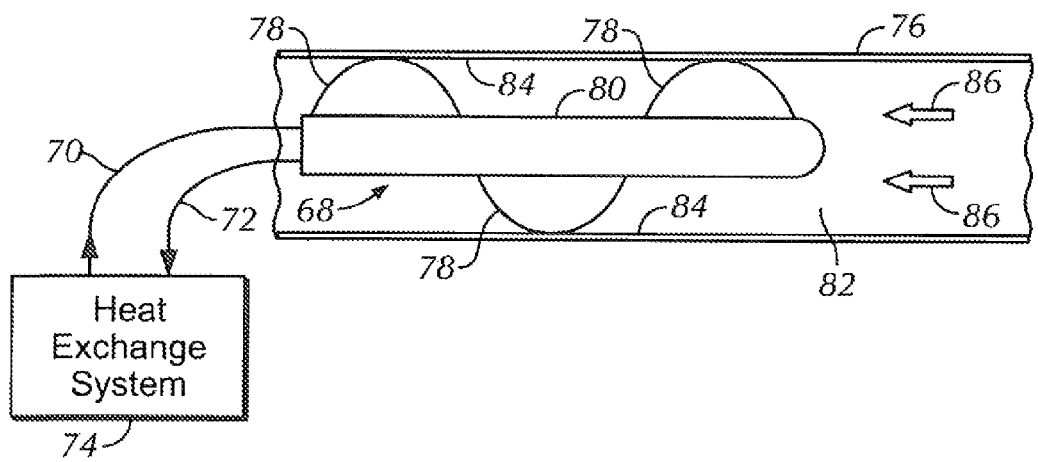
FIG. 7 is a schematic diagram of the non-limiting embodiment of the intravascular temperature management catheter of FIG. 6 while positioned in a patient.

Accordingly, the catheter 68 as shown in FIG. 7 still has the lumens 70 and 72 which are in fluid communication with the heat exchange system 74. The catheter 68 also has the wires 78 located generally longitudinally along the catheter 68 and engaged therewith, with only a one wire 78 engaged along a particular longitudinal portion of the heat exchange region 80.

Similar to FIG. 5, it may be appreciated from FIG. 7 that a portion of the wires 78 may expand against the walls 84 of the patient's blood vessel 82. Thus, blood may contact the heat exchange region(s) 80 as is passes the region(s) 80, as indicated by the blood-flow arrows 86, to exchange heat with the patient 76. However, in contrast to the embodiment of FIG. 5, the non-limiting embodiment shown in FIG. 7 has wires 78 alternating longitudinally along the heat exchange region 80 such that only one wire is engaged with only one portion of the heat exchange region 80 while still centering the heat exchange region 80 in the blood vessel 82.

Figure 8:
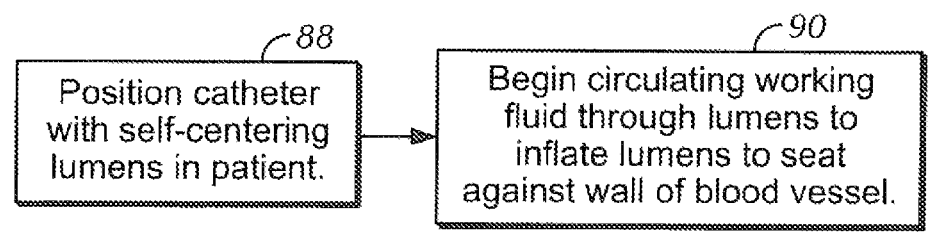
FIG. 8 is a flow-chart of method steps in accordance with present principles.

Moving on to FIG. 8, method steps in accordance with present principles are shown as a flow-chart. Beginning at block 88, a catheter having at least one self-centering lumen as disclosed herein is positioned in a patient so that the patient may be warmed or cooled. Then, at block 90, a heat exchange system fluidly connected to the catheter is activated to circulate working fluid through the lumens such that the lumens inflate to seat at least one large coil defined by one of the lumens against the wall of the blood vessel in which the catheter is positioned. At least one smaller coil also defined by at least one of the lumens is centered in the blood vessel. Blood may thus flow through the coil in accordance with present principles such that heat is transferred between the lumens and the blood.

While the particular SELF-CENTERING PATIENT TEMPERATURE CONTROL CATHETER is herein shown and described in detail, it is to be understood that the subject matter which is encompassed by the present invention is limited only by the claims.

What is claimed is:
1. A catheter, comprising:
working fluid supply and return lumens through which working fluid can circulate, at least one lumen being defined by plural coils axially spaced from each other, at least a first coil being a large coil that inflates with working fluid to seat against a wall of a blood vessel in which the catheter is positioned with blood flowing through the coil so as not to block blood flow in the vessel;
at least a second coil, the second coil being a small coil in that the second coil does not contact the wall of the blood vessel when inflated with working fluid; and at least a third coil, the third coil being a large coil that inflates with working fluid to seat against a wall of a blood vessel in which the catheter is positioned with blood flowing through the third coil so as not to block blood flow in the vessel, wherein the first and third coils are separated from each other in an axial dimension by the second coil.

2. The catheter of claim 1, wherein working fluid flows serially through the coils.

3. The catheter of claim 1, comprising a straight tube coaxial with the coils and in fluid communication therewith.

4. The catheter of claim 3, wherein the coils are in the working fluid supply path and the straight tube defines at least part of the working fluid return path.

5. The catheter of claim 4, wherein the coils are in the working fluid return path and the straight tube defines at least part of the working fluid supply path.

\* \* \* \* \*